United States Patent [19]

Maloney et al.

[11] Patent Number: 4,590,013

[45] Date of Patent: May 20, 1986

[54] PROCESS FOR PREPARING ALPHA ARYLACRYLONITRILES

[75] Inventors: John R. Maloney; Venkataraman Ramachandran, both of Baton Rouge, La.

[73] Assignee: Ethyl Corporation, Richmond, Va.

[21] Appl. No.: 735,151

[22] Filed: May 17, 1985

[51] Int. Cl.$^4$ .................. C07C 121/75; C07C 121/62; C07C 121/70
[52] U.S. Cl. ..................................... 558/332; 558/341
[58] Field of Search ............ 260/465 F, 465 G, 465 K

[56] References Cited

U.S. PATENT DOCUMENTS 4,536,343 8/1985 Ramachandran ............... 260/465 F

OTHER PUBLICATIONS

Jacobs et al., J. Org. Chem., vol. 48, pp. 5134–5135 (1983).

Primary Examiner—Dolph H. Torrence
Attorney, Agent, or Firm—Donald L. Johnson; John F. Sieberth; Patricia J. Hogan

[57] ABSTRACT

An alpha-arylacrylonitrile is prepared by reacting an aryl ketone having a removable hydrogen alpha to the carbonyl group with a cyanide ion source which is free of radicals that would stabilize a cyanohydrin corresponding to the aryl ketone and with a Lewis acid, preferably in the presence of a solvent. In a preferred embodiment, the aryl ketone is a tetralone, the cyanide ion source is hydrogen cyanide, the Lewis acid is aluminum chloride, and the product is a 1-cyano-3,4-dihydronaphthalene.

20 Claims, No Drawings

PROCESS FOR PREPARING ALPHA ARYLACRYLONITRILES

FIELD OF INVENTION

This invention relates to alpha-arylacrylonitriles and more particularly to a process for preparing them.

BACKGROUND

It is known that alpha-arylacrylonitriles are useful as chemical intermediates and that they can be prepared in various ways. For example, Jacobs et al., *Journal of Organic Chemistry*, 1983, Vol. 48, pp. 5134–5135, teach that 6-methoxy-1-cyano-3,4-di-hydronaphthalene is useful as an intermediate in the synthesis of steroids and that it can be prepared by (1) the addition of diethylaluminum cyanide to 6-methoxytetralone followed by dehydration or (2) the addition of cyanotrimethylsilane to 6-methoxytetralone followed by treatment with phosphoryl chloride in pyridine. As taught by Jacobs et al., the former method of synthesizing their alpha-arylacrylonitrile is impractical for large scale operations, and the latter method requires two steps.

Copending application Ser. No. 676,479, filed Nov. 29, 1984, now U.S. Pat. No. 4,536,343, in the name of V. Ramachandran, teaches that alpha-arylacrylonitriles can be prepared by reacting an aryl ketone having a removable hydrogen alpha to the carbonyl group with an alkali metal cyanide and aluminum chloride. Copending application Ser. No. 724,474, filed Apr. 18, 1985, in the names of Ramachandran, Davidson, and Maloney teaches that 6-alkoxy-1-cyano-3,4-dihydronaphthalenes can be prepared by reacting a 6-alkoxytetralone with a cyanide ion source which is free of radicals that would stabilize a cyanohydrin corresponding to the 6-alkoxytetralone and with a Lewis acid, optionally in the presence of a small amount of water and/or concentrated HCl.

SUMMARY OF INVENTION

An object of this invention is to provide a novel process for preparing alpha-arylacrylonitriles.

Another object is to provide such a process which is suitable for large scale operations and produces the alpha-arylacrylonitriles from aryl ketones in a single step.

These and other objects are attained by reacting an aryl ketone having a removable hydrogen alpha to the carbonyl group with a cyanide ion source which is free of radicals that would stabilize a cyanohydrin corresponding to the aryl ketone and with a Lewis acid.

DETAILED DESCRIPTION

Aryl ketones that can be used in the practice of the invention can be any aryl ketones having a removable hydrogen alpha to the carbonyl group. However, they are generally aryl ketones corresponding to the formula Ar—CO—R wherein Ar is aryl and R is a monovalent aliphatic, cycloaliphatic, or aromatic group having a removable hydrogen in the alpha-position. In such ketones the Ar group is generally an aryl group containing 6–20 carbons, most commonly a phenyl or naphthyl group which optionally bears one or more inert substituents, i.e., substituents that do not inhibit the activity of the Lewis acid in removing the removable hydrogen, such as alkyl, alkylthio, alkoxy, halo, nitro, etc. The R group is generally a saturated or unsaturated aliphatic, cycloaliphatic, or aromatic group containing 1–20 carbons, optionally bearing one or more inert substituents and sometimes joined with the Ar group to form a fused ring.

Exemplary of such ketones are phenyl alkyl ketones wherein the alkyl group is methyl, ethyl, propyl, isopropyl, butyl, isobutyl, t-butyl, pentyl, hexyl, heptyl, octyl, nonyl, decyl, dodecyl, etc.; the corresponding substituted-phenyl alkyl ketones wherein the substituents on the benzene ring may be any of the aforementioned alkyl groups and/or the corresponding alkoxy or alkylthio groups, chloro, bromo, nitro, etc.; the corresponding naphthyl or substituted-naphthyl alkyl ketones; the corresponding aryl substituted-alkyl ketones wherein the substituents on the alkyl group may be any of the aforementioned inert substituents; the corresponding aryl substituted-or-unsubstituted-cycloalkyl (e.g., cyclopropyl, cyclobutyl, cyclohexyl, cyclooctyl, etc.) ketones; the corresponding aryl substituted-or-unsubstituted-alkenyl ketones wherein the unsaturation is at least one carbon removed from the carbon bearing the removable hydrogen, such as ketones in which the alkenyl group is 2-butenyl, 3-hexenyl, 4-hexenyl, 4-octenyl, etc.; the corresponding aryl substituted-or-unsubstituted cycloalkenyl ketones; the corresponding aryl substituted-or-unsubstituted-aromatic ketones wherein said aromatic group is benzyl, phenylethyl, phenylpropyl, etc.; tetralone, etc. Among the preferred ketones are acetophenones, such as acetophenone, 4-chloroacetophenone, 4-isobutylacetophenone, 4-ethoxyacetophenone, etc., and tetralones, such as tetralone, 6-methoxytetralone, 7-bromotetralone, etc.

The Lewis acid utilized in the reaction may be any suitable Lewis acid, generally hydrogen fluoride, a trialkylaluminum, or, more preferably, a metal halide, such as boron or aluminum trifluoride, triiodide, trichloride, or tribromide, tin tetrachloride, zinc dichloride, gallium trichloride, titanium tetrachloride, diethylaluminum chloride, ethylaluminum dichloride, ethoxyaluminum dichloride, diethoxyaluminum chloride, hydroxyaluminum dichloride, dihydroxyaluminum chloride, and other such compounds wherein at least one halogen is attached to a metal atom, any remaining valences of which are usually satisfied by hydroxy, hydrocarbyl, or hydrocarbyloxy groups, generally hydroxy or alkyl or alkoxy groups containing 1–10 carbons. The preferred Lewis acids are boron trifluoride and aluminum chloride, especially aluminum chloride. This ingredient of the reaction mixture is ordinarily employed in the amount of about 0.5–1.5, preferably about 1–1.1, mols per mol of aryl ketone, although smaller or larger amounts can be employed if desired.

The cyanide ion that is reacted with the aryl ketone may be provided by any known source of cyanide ion which is free of radicals that would stabilize a cyanohydrin corresponding to the aryl ketone—a compound that is believed to be initially formed in the reaction. However, it is most commonly provided by hydrogen cyanide, a tri- or tetraalkylammonium cyanide (generally such a compound containing up to about 50 carbons) such as trimethylammonium cyanide, tributylmethylammonium cyanide, tetrabutylammonium cyanide, etc., or a metal cyanide, such as cuprous cyanide or an alkali or alkaline earth metal cyanide such as lithium, sodium, potassium, rubidium, cesium, beryllium, magnesium, calcium, strontium, or barium cyanide. The sodium, potassium, and hydrogen cyanides are generally the preferred sources of cyanide ion. The amount of cyanide ion employed is not critical, but it is usually desirable to employ about 1–5, preferably about 1–2, mols of cyanide ion per mol of aryl ketone to produce good yields of product.

Other ingredients that are suitably included in the reaction mixture are a solvent and a phase transfer catalyst. Solvents that may be employed include all solvents in which the reactants are soluble, such as aliphatic and aromatic hydrocarbons (e.g., toluene, xylenes, heptanes, and the like), chlorobenzene, nitrobenzene, etc.; but the preferred solvent is generally nitrobenzene. Particularly useful phase transfer catalysts are tetraalkylammonium halides (generally such halides containing up to about 50 carbons), preferably bromides and chlorides, such as tetrabutylammonium bromide, tributylmethylammonium chloride, etc. When employed, the catalyst is used in a catalytic amount, e.g., about 2–6% by weight of the aryl ketone; and its use sometimes seems to permit the attainment of higher yields than can be obtained in its absence.

In the practice of the invention, the ingredients of the reaction mixture may be combined in any suitable manner, preferably with the solids in finely-divided form, and heated at a suitable temperature, e.g., about 60°–120° C., preferably about 70°–90° C., to produce the desired product. Lower temperatures can be used but are less desirable because of their leading to slower reactions; higher temperatures are apt to be undesirable because of the tendency for by-products to be formed at the higher temperatures. The time required to obtain good yields varies with the temperature but is frequently in the range of about 4–10 hours.

It is sometimes preferred to combine the ingredients by prestirring the cyanide ion source, the Lewis acid, and a solvent before combining these ingredients with the aryl ketone, and it appears to be desirable to maintain the temperature of these ingredients below 60° C., e.g., at about 10°–50° C., conveniently at about 20°–30° C., until the addition of the aryl ketone has been completed.

It is also sometimes preferred to conduct the cyanation in the presence of a small amount of water and/or concentrated HCl —additives which appear to effect an activation of one or more of the reactants and increase yields. The particular amount of water and/or HCl employed is an activating amount, i.e., an amount insufficient to hydrolyze the Lewis acid completely, and may be provided simply by the water naturally present in one or more of the aforementioned ingredients of the reaction mixture. When it is desired to employ additional water and/or HCl, the added amount is generally in the range of about 0.1–1.0 mol per mol of the aryl ketone.

The process is a cyanation reaction which results in the formation of an alpha-arylacrylonitrile. When an aforementioned Ar—CO—R ketone is employed as the starting material, the product corresponds to the formula Ar—C(CN)=R′, wherein Ar has the same meaning as given above and R′ is the divalent group obtained by removing the removable hydrogen from R.

After completion of the reaction, the product can be recovered by conventional means or, alternatively, can be subjected to further reactions without being isolated when the further reactions would not be inhibited by impurities in the crude product. It is frequently desirable to subject the alpha-arylacrylonitrile to subsequent reactions. One such reaction is a dehydrogenation of a product such as 6-methoxy-1-cyano-3,4-dihydronaphthalene to a product such as 6-methoxy-1-cyanonaphthalene—a dehydrogenation that can be accomplished, e.g., by heating the reaction mixture, preferably at reflux temperatures, in the presence of a palladium-on-carbon catalyst or by other techniques known in the art.

The invention is particularly advantageous as a one-step, commercially-acceptable process for preparing alpha-arylacrylonitriles, especially 1-cyano-3,4-dihydronaphthalenes, that can then be converted to other products.

The following examples are given to illustrate the invention and are not intended as a limitation thereof.

EXAMPLE I

A mixture of 1.3 g of dry $AlCl_3$, 0.64 g of dry NaCN, and 87 mg of tetrabutylammonium bromide (TBAB) in 8.7 ml of dry nitrobenzene (NB) was stirred for two hours under a nitrogen atmosphere. Then 1.53 g of 6-methoxytetralone (6-MT) were added to provide a reaction mixture containing the 6-MT, NaCN, and $AlCl_3$ in a mol ratio of 1/1.5/1.1 and containing 5.6% of TBAB, based on the weight of 6-MT. The reaction mixture was stirred at 90° C. for 10 hours to form 6-methoxy-1-cyano-3,4-dihydronaphthalene (6-MCDN). After workup the VPC ratio of 6-MT/6-MCDN was determined to be 8/92. The process resulted in an 85% isolated yield of 6-MCDN.

EXAMPLE II

Example I was essentially repeated except that the $AlCl_3$/NaCN/TBAB/NB mixture was not subjected to the two hour stirring period prior to the addition of the 6-MT. After workup the VPC ratio of 6-MT/6-MCDN was determined to be 41/59.

EXAMPLE III

Example I was essentially repeated except that the 6-MT was replaced with 4-methoxyphenyl 3-chloropropyl ketone and the amount of NaCN was reduced to only 1.3 molar proportions. VPC analysis showed a 70% conversion of the ketone to alpha-(4-methoxyphenyl)-beta-(2-chloroethyl)acrylonitrile.

EXAMPLE IV

A mixture of 1.56 g of boron trifluoride etherate 0.98 g of NaCN, and 100 mg of TBAB in 10 ml of NB was stirred for two hours. Then 1.76 g of 6-MT were added to provide a reaction mixture containing the 6-MT, NaCN, and boron trifluoride in a mol ratio of 1/2/1.1. The mixture was heated at 90° C. for two hours and then at 120° C. for six hours to form 6-MCDN. Analysis showed the 6-MT/6-MCDN ratio to be 5/4.

EXAMPLE V

A solution of 22.7 g of anhydrous $AlCl_3$ in 100 ml of NB was cooled to 10° C. in an ice bath, after which 6.9 g of liquid HCN were added. The mixture was stirred vigorously and 30 g of 6-MT were added to provide a reaction mixture containing the 6-MT, HCN, and $AlCl_3$ in a mol ratio of 1/1.5/1. When the 6-MT had completely dissolved, the mixture was transferred to an autoclave and heated at 70° C. for ten hours. After cooling, the contents of the autoclave were removed and treated with 100 ml of dilute HCl and 100 ml of methylene chloride. The mixture was shaken in a separatory funnel and allowed to stand for phase separation. The lower organic layer was removed and concentrated on a rotary evaporator to remove methylene chloride. GC investigation (internal standard method) of the NB solution showed an 88% yield of 6-MCDN.

EXAMPLE VI

A crude 6-MCDN in NB prepared essentially as in Example I was treated with 5% (based on the weight of the original 6-MT) of 5% Pd/C at 150°–220° C. for 10 hours. The process resulted in the conversion of 97% of the 6-MCDN to 6-methoxy-1-cyanonaphthalene.

It obvious that many variations can be made in the products and processes set forth above without departing from the spirit and scope of this invention.

What is claimed is:

1. A process which comprises reacting an aryl ketone having a removable hydrogen alpha to the carbonyl group with a cyanide ion source, other than an alkali metal cyanide, which is free of radicals that would stabilize a cyanohydrin corresponding to the aryl ketone and with a Lewis acid.

2. The process of claim 1 wherein an aryl ketone corresponding to the formula Ar—CO—R is reacted with the cyanide ion source and Lewis acid so as to form an alpha-arylacrylonitrile corresponding to the formula Ar—C(CN)=R', in which formulas Ar is aryl, R is a monovalent aliphatic, cycloaliphatic, or aromatic group having a removable hydrogen in the alpha-position, and R' is the divalent group obtained by removing the removable hydrogen from R.

3. The process of claim 2 wherein the aryl ketone is an acetophenone.

4. The process of claim 3 wherein the acetophenone is 4-isobutylacetophenone.

5. The process of claim 2 wherein the aryl ketone is a tetralone.

6. The process of claim 5 wherein the tetralone is 6-methoxytetralone.

7. The process of claim 1 wherein the cyanide ion source is hydrogen cyanide, a tri- or tetraalkylammonium cyanide, or a metal cyanide.

8. The process of claim 7 wherein the cyanide ion source is hydrogen cyanide.

9. The process of claim 7 wherein the cyanide ion source is a metal cyanide.

10. The process of claim 7 wherein the cyanide ion source is an alkaline earth metal cyanide.

11. The process of claim 1 wherein the Lewis acid is a metal halide.

12. The process of claim 11 wherein the metal halide is aluminum chloride.

13. The process of claim 1 wherein the reaction is conducted in the presence of a catalytic amount of a phase transfer catalyst.

14. The process of claim 13 wherein the catalyst is a tetraalkylammonium halide.

15. The process of claim 14 wherein the tetraalkylammonium halide is tetrabutylammonium bromide.

16. The process of claim 1 wherein the reaction is conducted in a solvent.

17. The process of claim 16 wherein the solvent is nitrobenzene.

18. The process of claim 1 wherein the reaction is conducted at a temperature of about 60°–120° C.

19. A process which comprises reacting a tetralone having a removable hydrogen alpha to the carbonyl group with hydrogen cyanide and aluminum chloride at a temperature of about 60°–120° C. so as to form a 1-cyano-3,4-dihydronaphthalene.

20. The process of claim 19 wherein the tetralone is 6-methoxyteralone and the product is 6-methoxy-1-cyano-3,4-dihydronaphthalene.

* * * * *